US012770727B2

(12) United States Patent
Lee

(10) Patent No.: US 12,770,727 B2
(45) Date of Patent: Oct. 20, 2026

(54) METHODS FOR PREDICTING SAFETY AND EFFECTIVENESS OF SPINAL THERMAL DEVICES

(71) Applicants: CERAGEM Co., Ltd., Cheonan-si (KR); CERAGEM CLINICAL, INC., Seoul (KR)

(72) Inventor: Kiwon Lee, Hanam-si (KR)

(73) Assignees: Ceragem Co., Ltd., Cheonan-si (KR); Ceragem Clinical, Inc., Seoul (KR)

( * ) Notice: Subject to any disclaimer, the term of this patent is extended or adjusted under 35 U.S.C. 154(b) by 575 days.

(21) Appl. No.: 18/359,742

(22) Filed: Jul. 26, 2023

(65) Prior Publication Data

US 2024/0062868 A1 Feb. 22, 2024

(30) Foreign Application Priority Data

Aug. 16, 2022 (KR) ........................ 10-2022-0102107

(51) Int. Cl.

*G16H 20/30* (2018.01)
*A61H 1/02* (2006.01)
*G16H 40/60* (2018.01)
*G16H 50/30* (2018.01)
*G16H 50/50* (2018.01)

(52) U.S. Cl.

CPC ........... *G16H 20/30* (2018.01); *A61H 1/0218* (2013.01); *G16H 40/60* (2018.01); *G16H 50/30* (2018.01); *G16H 50/50* (2018.01); *A61H 2201/0207* (2013.01)

(58) Field of Classification Search

None

See application file for complete search history.

(56) References Cited

FOREIGN PATENT DOCUMENTS

| | | | | | |
|---|---|---|---|---|---|
| CN | 105943228 | A | * | 9/2016 | ........... A61H 1/0296 |
| CN | 107997866 | A | * | 5/2018 | ........... A61H 9/0078 |
| JP | 2013-153876 | A | | 8/2013 | |
| JP | 2019-517886 | A | | 6/2019 | |
| JP | 2022-100549 | A | | 7/2022 | |
| KR | 10-2013-0044791 | A | | 5/2013 | |
| KR | 10-2011-0070736 | A | | 6/2014 | |
| KR | 10-2015-0059244 | A | | 6/2015 | |
| KR | 10-1992384 | B | | 6/2019 | |
| KR | 101992384 | B1 | * | 6/2019 | ............. A61H 15/02 |

(Continued)

OTHER PUBLICATIONS

Machine translation of Xei et al. (Year: 2019).*

(Continued)

*Primary Examiner* — Matthew G Marini

(74) *Attorney, Agent, or Firm* — Knobbe, Martens, Olson & Bear, LLP

(57) ABSTRACT

A method for predicting safety and effectiveness of a spinal thermal device may include generating three-dimensional structure data of a user's body, generating three-dimensional structure data of the spinal thermal device, setting a set value of the spinal thermal device, calculating a stress applied to the user's body and a strain of the user's body in a process of pressurizing the user's body as the spinal thermal device operates as the set value, converting a strain value of a user's body to a degree of traction, and visualizing the degree of traction of the user's body.

8 Claims, 10 Drawing Sheets

(56) References Cited

FOREIGN PATENT DOCUMENTS

| | | | |
|---|---|---|---|
| KR | 10-2279549 | B1 | 7/2021 |
| KR | 10-2021-0112847 | A | 9/2022 |

OTHER PUBLICATIONS

Machine translation of Wang (Year: 2018).*

Cardoso et al., "Computational modeling of posteroanterior lumbar traction by an automated massage bed: predicting intervertebral disc stresses and deformation," Front. Rehabilit. Sci. (Aug. 1, 2022).

Park, et al., "Biomechanical analysis of two-step traction therapy in the lumbar spine," Manual Therapy, vol. 19, No. 6, pp. 527-533, Dec. 2014.

Yoon et al., "Mechanical Changes of the Lumbar Intervertebral Space and Lordotic Angle Caused by Posterior-to-Anterior Traction," Health Care, MDPI, vol. 9, 900, pp. 1-10, Jul. 15, 2021.

Notice of Allowance in KR Patent Application No. 10-2022-0102107 dated Aug. 21, 2023.

Office Action received in IN Patent Application No. 202314050503 dated Sep. 12, 2025.

Office Action received in Japanese Application No. 2023-123953 dated Aug. 27, 2024.

* cited by examiner (b)

(a)

METHODS FOR PREDICTING SAFETY AND EFFECTIVENESS OF SPINAL THERMAL DEVICES

CROSS-REFERENCE TO RELATED APPLICATION

This application claims priority to and the benefit of Korean Patent Application No. 10-2022-0102107, filed on Aug. 16, 2022, the disclosure of which is incorporated herein by reference in its entirety.

FIELD

The present disclosure relates to a method for predicting safety and effectiveness of a massage device, and more particularly, to a method for predicting safety and effectiveness of a spinal thermal device.

BACKGROUND

The spinal traction is a physical treatment that provides a constant or intermittent stretching axial force to the lumbar spine to disperse the spinal tissue into better alignment, reduces pressure in an intervertebral disc (IVD), and manages lower back pain (LBP).

The spinal traction device may draw the users spine by applying an axial (length) traction force to the spine in a direction of the user's craniocaudal, however, the axial traction may change a normal lordotic curvature or reduce a lumber lordotic angle, and may potentially cause, for example, muscle pain, cramps, joint or ligament damage, and insufficient pressure reduction in the intervertebral disc.

In addition, when the spinal traction is performed without considering the user's body type (normal, overweight, moderate obese, severe obese, etc.), the traction effect may become inconsistent, and when the spine is pulled too much to improve the traction effect, there is a risk that the user may be injured.

Therefore, there is a need for a technology capable of optimizing the traction effect provided through a spinal thermal device.

The disclosure of this section is to provide background information relating to the present disclosure. Applicant does not admit that any information contained in this section constitutes prior art.

SUMMARY

The present disclosure is to provide a traction effect while rising from rearward to frontward (posteroanterior, PA) along a height direction using a spinal thermal device, and optimizes the traction effect according to a body shape of a user, thereby providing a method for predicting safety and effectiveness of the spinal thermal device.

The disclosure is not limited to the above-described tasks, and other tasks not described herein will be clearly understood by those skilled in the art from the following description.

According to an aspect of the disclosure, there is provided a method of predicting safety and effectiveness of a spinal thermal device, the method including: generating three-dimensional structure data of a user's body, generating three-dimensional structure data of the spinal thermal device, setting a set value of the spinal thermal device, calculating a stress applied to the user's body and a strain of the user's body in a process of pressurizing the user's body as the spinal thermal device operates as the set value, converting a strain value of a user's body to a degree of traction, and visualizing the degree of traction of the user's body.

In this case, the calculating the stress applied to the user's body and the strain of the user's body in the process of pressurizing the user's body may include: visualizing the stress and the strain of the user's body.

In this case, the calculating the stress applied to the user's body and the strain of the user's body in the process of pressurizing the user's body may include: calculating the stress applied to the user's body and the strain of the user's body while the user's body is strained along a length direction as a ceramic of the spinal thermal device rises along the height direction.

In this case, the calculating the stress applied to the user's body and the strain of the user's body in a process of pressurizing the user's body may include: calculating the stress and strain of a portion corresponding to the depth of the user's spine while the user's body is strained along a length direction as a ceramic of the spinal thermal device rises along the height direction.

In this case, the converting the strain value of the user's body to a degree of traction may include: correcting the strain value of the user's body by reflecting the spine distance data for each body position of the user.

In this case, the calculating the stress and the strain of the user's body may include: calculating the stress and the strain of the user's body through a dynamic explicit formulation.

In this case, the setting the set value of the spinal thermal device may include: setting a ceramic temperature, a ceramic height, and a heating element temperature.

In this case, the method may further include: after the visualizing the degree of traction of the user's body, deriving the set value for obtaining an optimal traction effect within a range of the set ceramic temperature, ceramic height, and heating element temperature.

In this case, the deriving the set value for obtaining the optimal traction effect may include: deriving the set value for obtaining an optimal traction effect for each user's body type according to a change in structure according to the user's body type.

In this case, the three-dimensional structure data of the user's body may be three-dimensional structure data classified into skin, subcutaneous fat, soft tissue, muscles, vertebrae, intervertebral disc, epidural fat, cerebrospinal fluid, and spinal cord.

According to the above configuration, the method for predicting the safety and effectiveness of the spinal thermal device according to the embodiment of the disclosure generates three-dimensional structure data of a user's body, generates three-dimensional structure data of the spinal thermal device, and calculates stress applied to the user's body and strain of the user's body during the operation of the spinal thermal device according to the set value and then converts the stress and strain into a traction degree, thereby optimizing the traction effect according to the user's body type, thereby predicting the safety and effectiveness of the spinal thermal device.

It should be understood that the effects of the disclosure are not limited to the above-described effects, and include all effects that can be inferred from the configuration of the disclosure described in the detailed description or claims of the disclosure.

DETAILED DESCRIPTION

Figure 1:
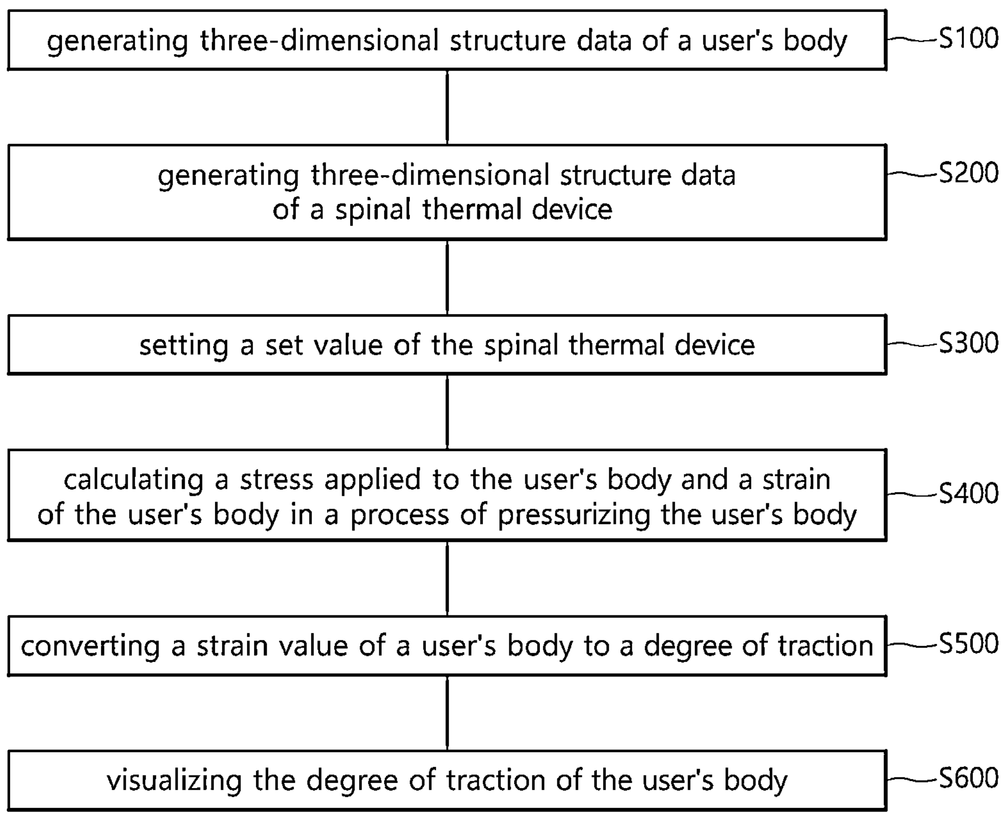
FIG. 1 is a flowchart illustrating a method for predicting safety and effectiveness of a spinal thermal device according to an embodiment of the present disclosure.

Hereinafter, embodiments of the present disclosure will be described in detail with reference to the accompanying drawings so that those skilled in the art can easily carry out the present disclosure. The present disclosure may be embodied in various different forms and is not limited to the embodiments described herein. In order to clearly describe the present disclosure, parts not related to the description are omitted in the drawings, and the same or similar components are denoted by the same reference numerals throughout the specification.

The words and terms used in the specification and the claims are not interpreted as limited to ordinary or dictionary meanings, but should be interpreted as meanings and concepts corresponding to technical aspects of the present disclosure according to principles capable of defining terms and concepts by the inventor in order to describe the disclosure in the best way.

Figure 2:
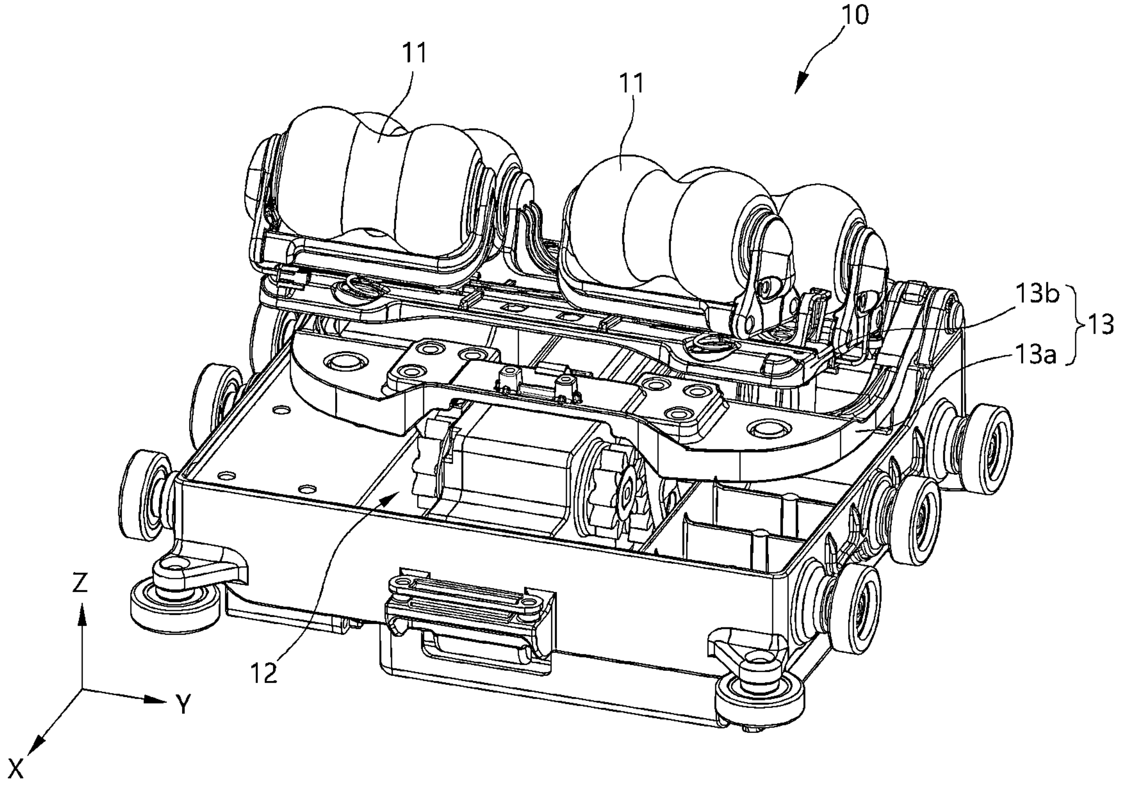
FIG. 2 is a perspective view illustrating a spinal thermal device according to an embodiment of the present disclosure.
Figure 3:
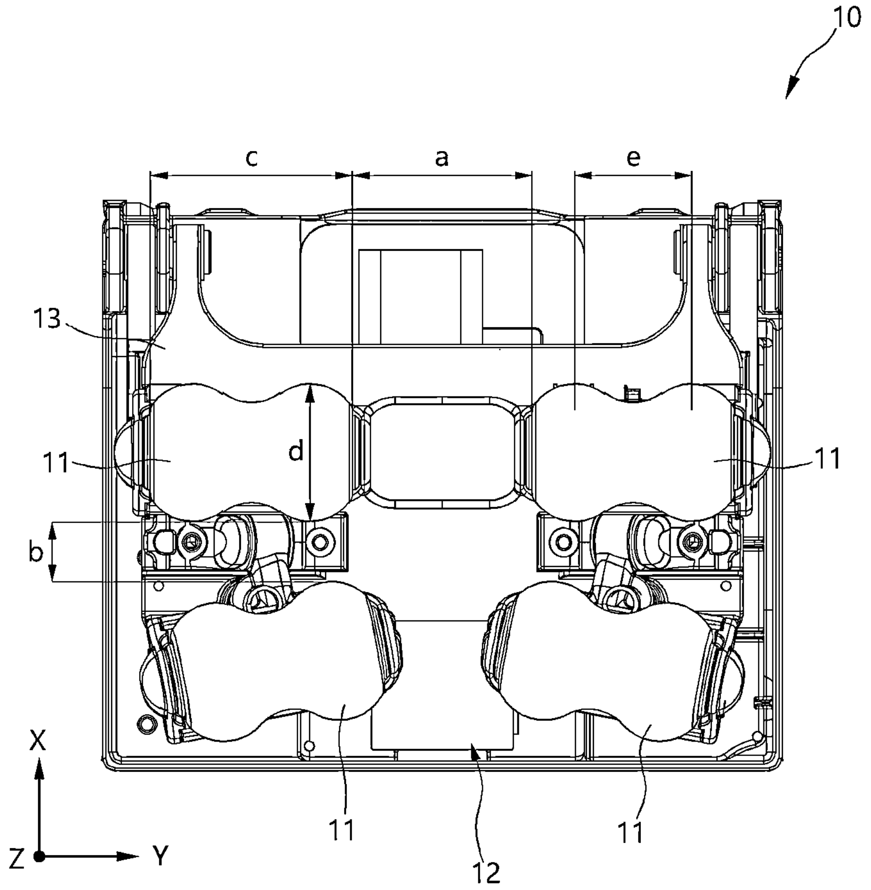
FIG. 3 is a plan view illustrating a spinal thermal device according to an embodiment of the present disclosure.
Figure 4:
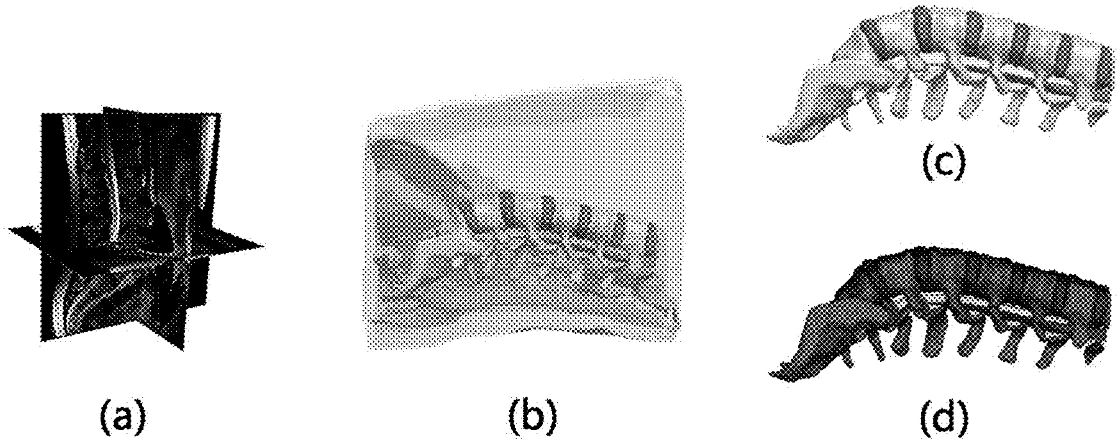
FIG. 4 is a view showing a lower back model of user, (a) shows the result of MRI scan of lower back of a normal BMI user, (b) shows segmentation of tissues, (c) shows 3D rendering of lumbar discs and spine, and (d) shows finite element mesh of the lumbar disc and the spine.
Figure 5:
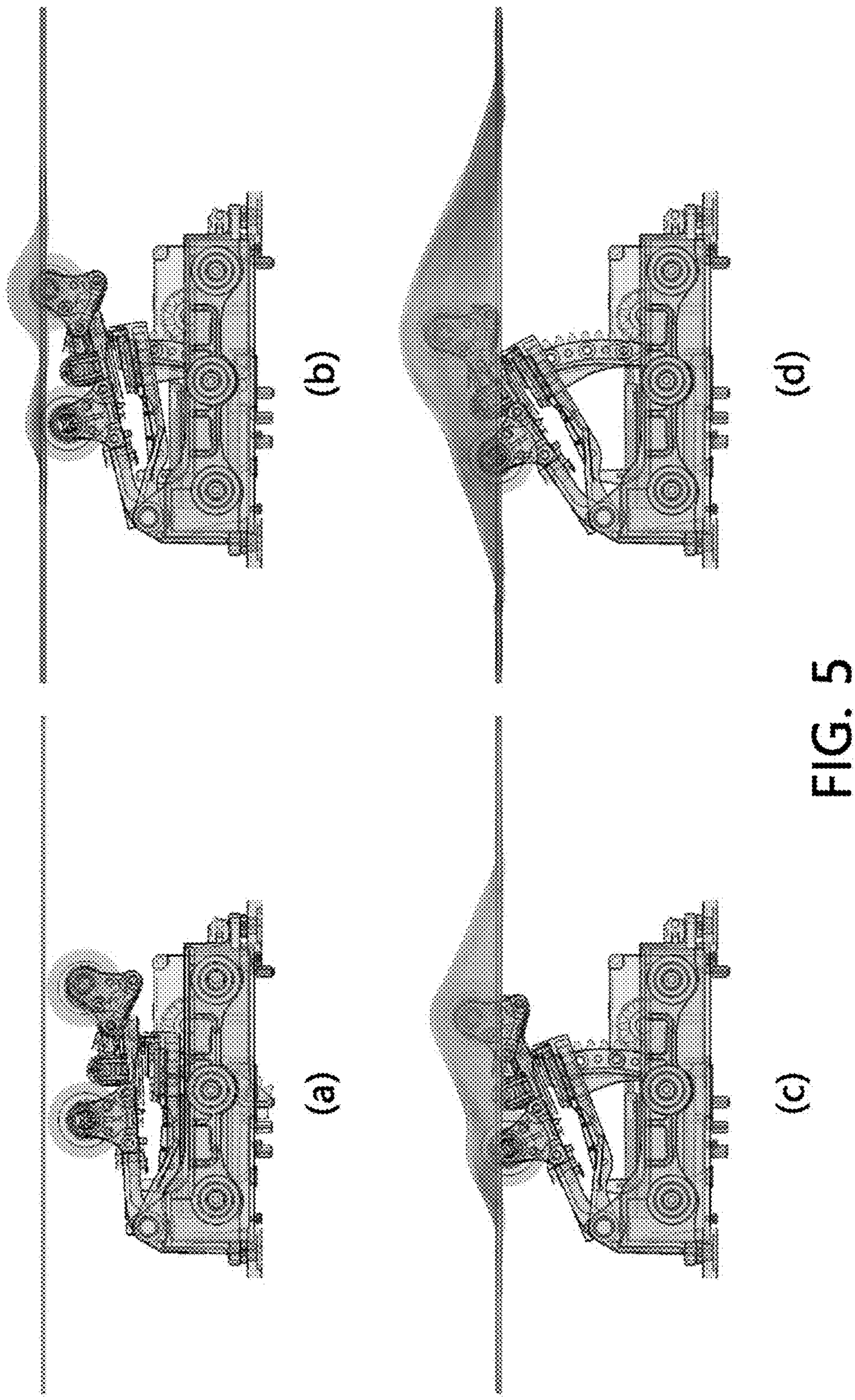
FIG. 5 is a view illustrating a spinal thermal device and a bed mat layer according to an embodiment of the present disclosure, showing a vertical position of a ceramic at various traction levels, (a) shows resting position of the ceramic, (b) shows vertical displacement of the ceramic at traction level 3 (TL3), (c) shows position of the ceramic and bed mat at traction level 6 (TL6), and (d) shows maximum height reached by the ceramic at traction level 9 (TL9), corresponding to ~62 mm above resting position.

FIG. 1 is a flowchart illustrating a method for predicting safety and effectiveness of a spinal thermal device according to an embodiment of the present disclosure, FIG. 2 is a perspective view illustrating a spinal thermal device according to an embodiment of the present disclosure, FIG. 3 is a plan view illustrating a spinal thermal device according to an embodiment of the present disclosure, FIG. 4 is a diagram showing a lower back model of user, (a) shows the result of MRI scan of lower back of a normal BMI user, (b) shows segmentation of tissues, (c) shows 3D rendering of lumbar discs and spine, and (d) shows finite element mesh of the lumbar disc and the spine, FIG. 5 is a diagram illustrating a spinal thermal device and a bed mat layer according to an embodiment of the present disclosure, showing a vertical position of a ceramic at various traction levels, (a) shows resting position of the ceramic, (b) shows vertical displacement of the ceramic at traction level 3 (TL3), (c) shows position of the ceramic and bed mat at traction level 6 (TL6), and (d) shows maximum height reached by the ceramic at traction level 9 (TL9), corresponding to ~62 mm above resting position, at this time, the X axis means a direction in which the spinal thermal device moves along a user's body to thermally massage the user in a longitudinal direction (axial direction), the Y axis means a direction in which the spinal thermal device moves along a lateral direction of the user in a width direction, and the Z axis means a direction in which the spinal thermal device moves upward to press the user in a height direction. In order to clearly describe the present disclosure, parts not related to the description are omitted in the drawings.

As shown in FIG. 1, according to an embodiment of the present disclosure, there is provided a method for predicting safety and effectiveness of a spinal thermal device, the method including generating three-dimensional structure data of a user's body using a computer (Step 100), generating three-dimensional structure data of the spinal thermal device 10 (Step 200), setting a set value of the spinal thermal device 10 (Step 300), calculating a stress applied to the user's body and a strain of the user's body in a process of pressurizing the user's body as the spinal thermal device 10 operates as the set value (Step 400), converting a strain value of a user's body to a degree of traction (Step 500), and visualizing the degree of traction of the user's body (Step 600).

At this time, the computer may include a notebook, a laptop, a tablet PC, a slate PC, and the like equipped with a web browser (WEB Browser), and the computer may comprise a controller for performing each of the above steps, an input unit for inputting a user command, and an output unit for showing a resultant to the user.

The controller may include a processor, a ROM in which a control program is stored, and a RAM that stores an input signal or data or is used as a storage area corresponding to various operations to be performed.

In addition, a graphic processing board including a processor, a RAM, or a ROM may be included in a separate circuit board electrically connected to the controller. The processor, the RAM, and the ROM may be connected to each other through an internal bus.

In addition, the controller may be used as a term referring to a component including the processor, the RAM, and the ROM. Also, the controller may be used as a term referring to a component including the processor, the RAM, the ROM, and the processing board.

The input unit receives a predetermined instruction or command from a user for controlling the computer. For example, the input unit may include a user interface such as a keyboard, a mouse, a trackball, a time gain compensation (TGC) control knob, a lateral gain compensation (LGC) control knob, or a paddle.

The output unit may display a resultant on one or more display areas. The user may check the visualized result through the display area.

In this case, data related to the user's body may be pre-held user's body data, and may be computed tomography (CT) or magnetic resonance imaging (MRI) data. Also, the user's body data may be three-dimensional structure data classified into skin, subcutaneous fat, soft tissue, muscles, vertebrae, intervertebral disc, epidural fat, cerebrospinal fluid, and spinal cord. When the user's body data is modeled and simulated as described above, safety and effectiveness for various user's body types can be predicted. In other words, the stress and strain vary according to a BMI value, and at the same time, whether there is a risk of injury may be varied, and the stress and strain capable of providing an optimal traction effect depending on the BMI value can be derived through this, and when the stress and strain are reflected into the spinal thermal device 10, not only the optimal traction effect can be provided to various users but also the precaution to avoid injuries can be delivered.

A T2-weighted MRI of a healthy male adult (BMI: 25 kg/$m^2$, age: 42 years) was performed by using a 3 T Siemens MAGNETOM Prisma scanner equipped with a CP Spine array coil (Siemens Healthineers, PA, USA), and parameters of image acquisition was set according to: TE=99 ms, TR=7,040 ms, flip angle=130°, FOV=256 mm, SNR=1, in-plane resolution=256×256, slice thickness=1 mm, and voxel size: 1×1×1 mm.

The MRI was segmented into nine tissue masks: skin, subcutaneous fat, soft tissue, muscles, intervertebral disc, vertebrae, epidural fat, cerebrospinal fluid, and spinal cord. Manual tissue segmentation was carried out by first thresholding the images, followed by morphological filtering such as flood fill, dilation, and erosion, performed in Simpleware ScanIP (Synopsys Inc., CA, USA). Through thorough review and adjustment, the most advanced precision of the user subject's spine and surrounding tissues was ensured.

The normal BMI user's subcutaneous fat (thickness: 13 mm) was further artificially dilated to generate users with different BMI values, namely overweight (25<BMI<30; thickness: 26 mm), moderate obese (30<BMI<40; thickness: 52 mm), and extreme obese (40<BMI<65; thickness: 86 mm) (46). For the dilation procedure, the subcutaneous fat of the normal BMI spine model was first merged with the skin, then dilated isometrically to the aforementioned fat thickness, and later the skin mask was recovered by further dilating the merged mask by the original thickness of the skin (~1 mm) to form the new skin mask.

The four BMI user subject models were meshed in Simpleware ScanIP using an adaptive tetrahedral voxel-based meshing algorithm into a finer mesh. The resulting normal BMI model is consisted of >3.36 M tetrahedral elements, the overweight BMI model is consisted of >3.43 M elements, the moderate obese model is consisted of >3.46 M elements, and the extreme obese model is consisted of >3.68 M elements. The four models were later imported into Abaqus (v.2019, Dassault Systems, MA, USA) to computationally solve the finite element method (FEM) model.

The spinal thermal device 10 (Master 4, CGM MB-1901, CERAGEM Co. Ltd., Cheonan) that provides posteroanterior traction, was applied using numerical modeling. The spinal thermal device 10 was imported into Abaqus (v.2019, Dassault Systems, MA, USA) for positioning of its parts, creating the rotary linkages (hinges) of several movable components and it was meshed using an adaptive tetrahedral voxel-based meshing algorithm. The spinal thermal device 10 can move horizontally along the length direction X, which is the craniocaudal direction of the patient laying on supine position on the device bed. In addition, the spinal thermal device 10 is composed of four massage ceramics 11 located under the device mat, the four ceramics 11 are arranged at the vertices of a rectangle. A width direction Y distance (a) between the ceramics 11 is 56 mm, and a length direction X distance (b) between top and bottom ceramics 11 is 32 mm A width (c) of the four ceramics 11 is 65 mm, a diameter of the circular ends (d) is 45 mm, and a spacing (e) between the two circular ends is 30 mm.

The spinal thermal device 10 may include a driving unit 12 for adjusting the position of the ceramics 11 in the length direction X, and a support unit 13 for supporting the ceramics 11. The support unit 13 may include a first support member **13*a* for supporting the ceramics 11 disposed on one side of the length direction X and a second support member 13*b* for supporting the ceramics 11** disposed on the other side of the length direction X.

After generating the three-dimensional structure data of the spinal thermal device 10 as described above, the set value of the spinal thermal device 10 is set. The set value may be a temperature of the ceramics 11 according to the thermal massage mode selected by the user, a height of the ceramics 11, a temperature of the heating element, and the like.

Thereafter, as the set value, as the spinal thermal device 10 operates, stress applied in a process of pressing of the user's body and strain rate of the user's body are calculated. In this case, the stress and strain rate of the skin, muscle, vertebrae, intervertebral disc of the user may be calculated.

The ceramics 11 move vertically along the height direction Z to identify the curvature of the user's spine. The ceramics 11 then moves to specific locations in lumbar or cervical regions of the user's spine and gradually lift massage rollers in the height direction Z. The vertical displacement of the ceramics 11 is controlled by a traction level (TL) setting of the system. The full range of motion is divided in 9 consecutive TL values, where the vertical displacement of the ceramics 11 is increased by approximately 6.9 mm at each traction level, resulting in a maximal vertical displacement of 62 mm at TL9. FIG. 5 shows the spinal thermal device and the bed mat at the initial position (FIG. 5(A)) and at three different vertical position levels ((b), (c) and (d) of FIG. 5) corresponding to traction level 3, 6, and 9, respectively.

An assembly was created in Abaqus between the user subject model and the spinal thermal device 10. The user subject model was positioned directly above the spinal thermal device 10 and the bed mat, with a clearance of 0.1 mm A contact condition was implemented between the surface of the ceramics 11 and the bottom surface bed mat, and a second contact condition was implemented between the top surface of the bed mat and the bottom (posterior side) surface of the user subject. The ceramics 11 and the top of the bed mat were defined as master surfaces, and in turn, the bottom of the bed mat and the skin in the user subject's back were identified as slave surfaces for the contact condition. The contact between these surfaces was defined as frictionless in a tangential direction and as "hard contact" in a normal direction. A set of nodes were selected on the top and bottom, anterior-aspect of the user subject, and defined as a boundary condition with zero translation in three spatial coordinates, but free to rotate in any direction. Each tissue constituent was assigned linear elastic material properties: (1) skin (E=160 MPa; ν=0.49; ρ=1,020 kg $m^{-3}$), (2) muscle (E=7 MPa; ν=0.49; ρ=1,100 kg $m^{-3}$), (3) soft tissue (E=23.5 MPa; ν=0.49; ρ=1,057 kg $m^{-3}$), (4) vertebrae (E=17 GPa; ν=0.30; ρ=1,800 kg $m^{-3}$), (5) intervertebral disc (E=17 MPa; ν=0.49; ρ=1,100 kg $m^{-3}$), (6) subcutaneous fat/epidural fat: (E=3 MPa; ν=0.49; ρ=920 kg $m^{-3}$), (7) CSF: (K=2.25 GPa; ν=0.499; ρ=1,000 kg $m^{-3}$), (8) spinal cord/dura mater: (E=10 MPa; ν=0.49; ρ=1057 kg $m^{-3}$). A dynamic explicit formulation was used to solve for the deformation, stresses and strains produced in the user subject model by the displacement of the ceramics 11.

Figure 6:
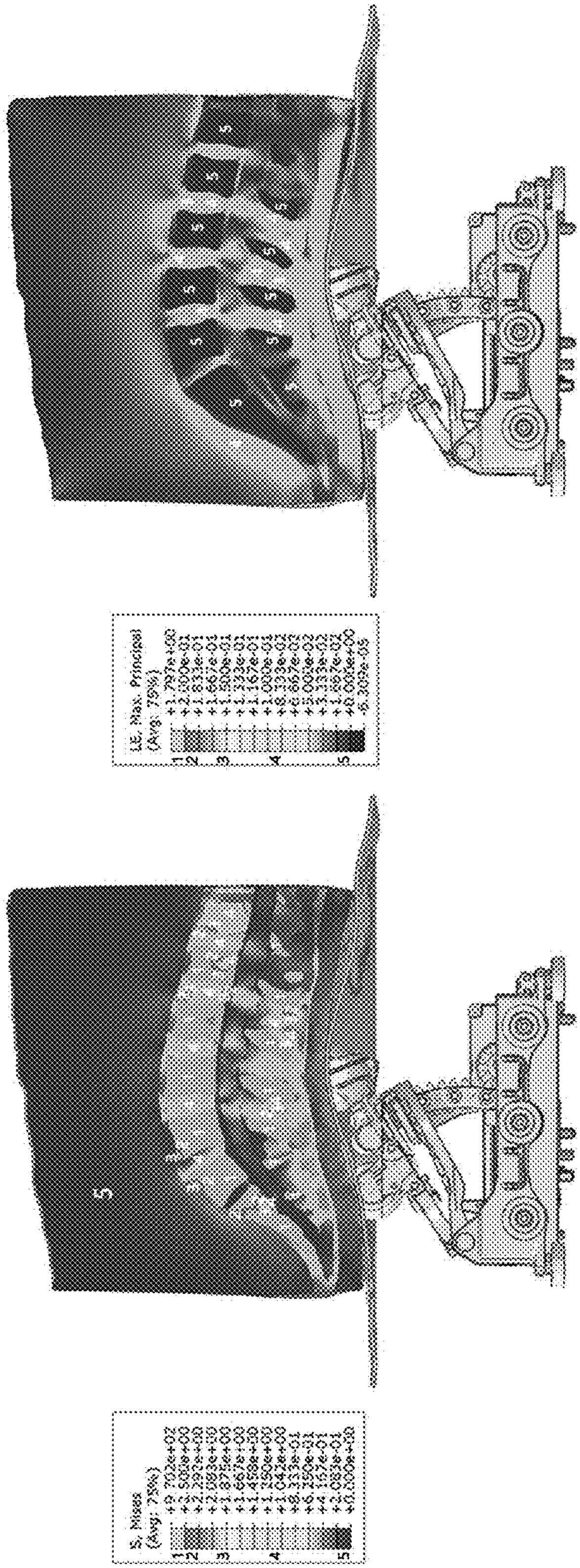
FIG. 6 is a view illustrating a spinal thermal device and a model assembly according to an embodiment of the present disclosure, (a) shows the applied stresses and (b) depicts the strains produced by posteroanterior traction produced by the spinal thermal device on the tissues of a normal BMI user.

FIG. 6 is a diagram showing a spinal thermal device and a model assembly according to an embodiment of the present disclosure, in which (a) shows the applied stress, (b) shows the strains produced by posteroanterior traction produced by the spinal thermal device on the tissues of a normal BMI user subject.

A mid-sagittal view of the effect produced by mechanical actuation on the tissues of the normal BMI subject model at traction level 9 is shown in FIG. 6, it can be seen that a first support member 13*a* disposed on one side (front) in the length direction produces the greatest deformation on the skin and fatty tissues layer, as well as maximal traction directly under the location of the vertebral bodies L2 to L4. The 3D stresses are depicted in FIG. 3(A) and the strains in FIG. 3(B). This result shows that the largest stresses and deformation occurs at the center of the lumbar spine, at the level of the L2-L4 vertebral bodies. The stress plot shows von Mises stresses, demonstrating the heterogeneity of stresses in the lower back under the action of the mechanical traction. As expected, the highest stresses and smallest deformations occur at the vertebral bodies, since calcified tissues have the highest elastic modulus. The internal stresses in the intervertebral discs increase as a function of traction level. These stresses counteract the compression stress level in the disc prior to the mechanical traction.

Figure 7:
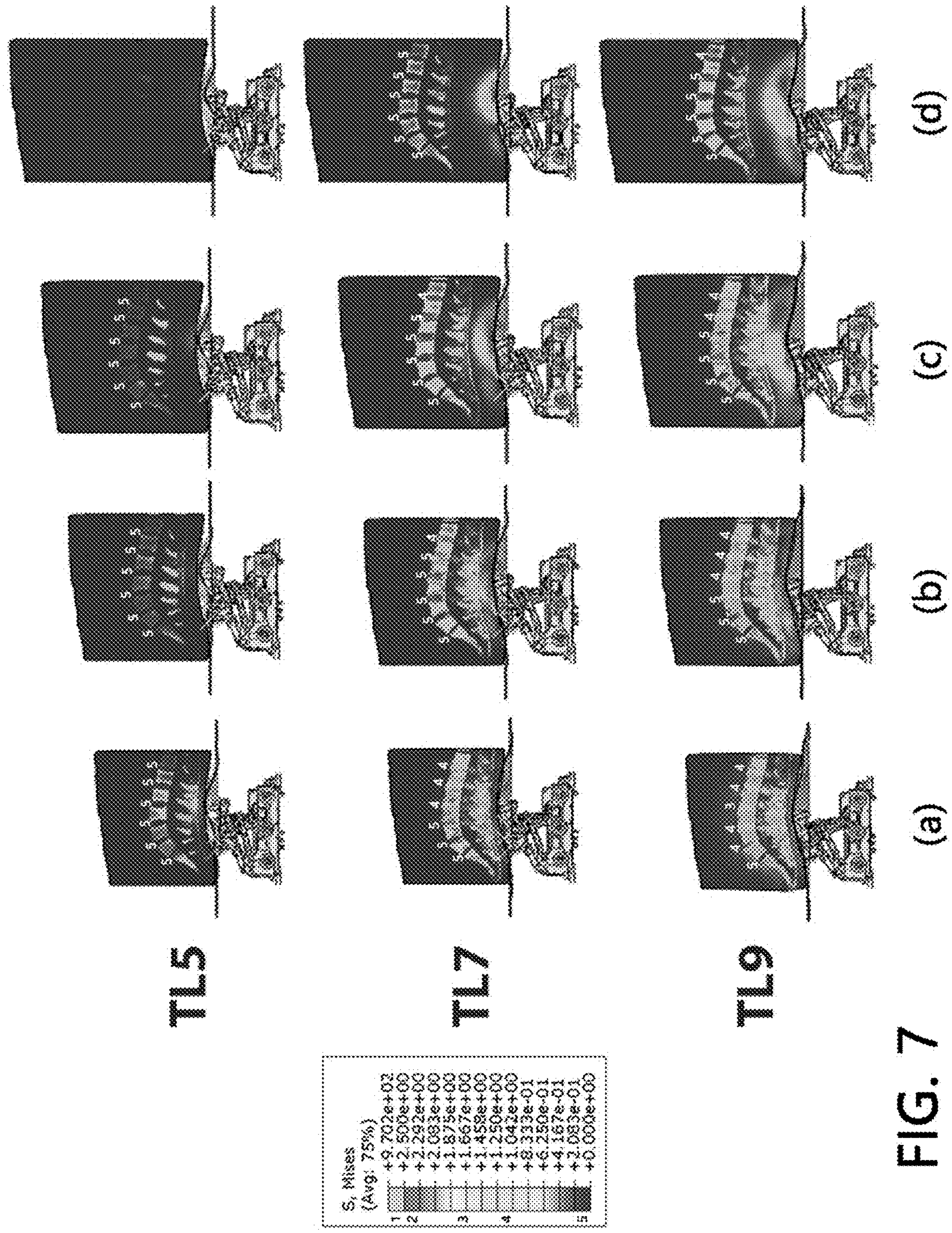
FIG. 7 is a view showing 3D stress for different BMI models, (a) shows the stress at traction levels 5, 7 and 9 for normal BMI user model, (b) shows the stress at traction levels 5, 7 and 9 for an overweight BMI user model, (c) shows the stress at traction levels 5, 7 and 9 for moderate obese BMI user model, and (d) shows the stress at traction levels 5, 7 and 9 for severe obese BMI user model.

FIG. 7 is a diagram showing 3D stress for different BMI models, (a) shows the stress at traction levels 5, 7 and 9 for normal BMI user model, (b) shows the stress at traction levels 5, 7 and 9 for an overweight BMI user model, (c) shows the stress at traction levels 5, 7 and 9 for moderate obese BMI user model, and (d) shows the stress at traction levels 5, 7 and 9 for severe obese BMI user model.

3D stress at traction levels 5, 7 and 9 (row panels) for normal, overweight, moderate obese and severe obese (column panels) users is shown in FIG. 7. It can be seen that the highest stress occurs in the normal BMI model at the highest traction level. The effect of mechanical traction can also be confirmed in overweight, moderate obese, and severe obese models, but the relative intensity of the stress decreases as a function of BMI. Analysis of the 3D stress maps of the lumbar discs and spine of different BMI models demonstrate that the effect of mechanical traction is evident in all models. The normal BMI is the model with the highest stress relief in the lumbar discs, and the intensity of stress relief is inversely proportional to the BMI in the model. Still the mechanical traction of the spinal thermal device is present even in the severe obese BMI model.

Figure 8:
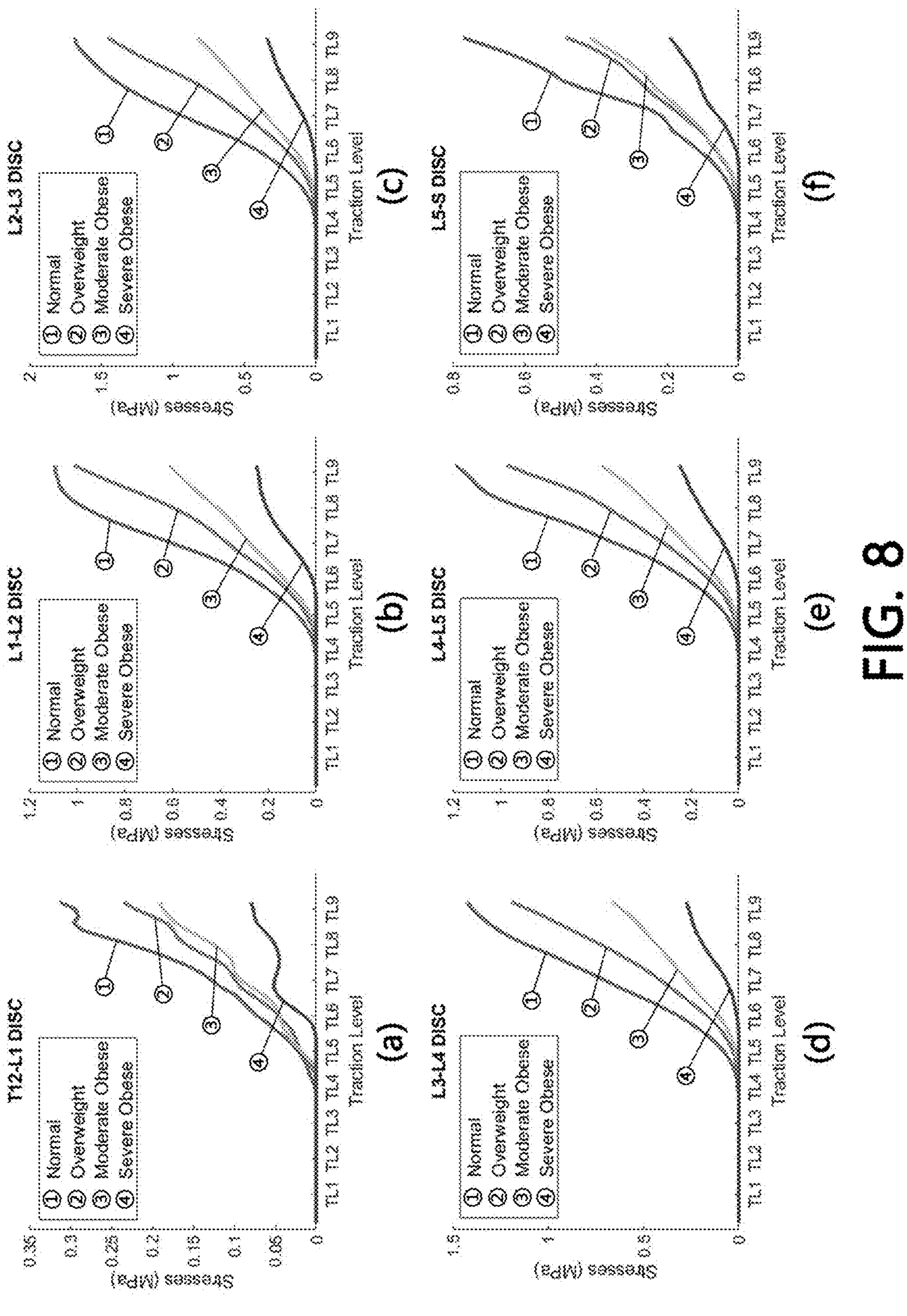
FIG. 8 is a view quantitatively comparing average stresses on different BMI models, (a) to (f) are diagrams showing average stresses according to traction levels (TL1-9) for each lumbar disc location, classified according to BMI (normal, overweight, moderate obese, and severe obese).

FIG. 8 is a diagram quantitatively comparing average stresses on different BMI models, (a) to (f) are diagrams showing average stresses according to traction levels (TL1-9) for each lumbar disc location, classified according to BMI (normal, overweight, moderate obese, and severe obese).

FIG. 8 shows the function of traction level (TL1-9) for normal, overweight, moderately obese and extreme obese. These curves were obtained by averaging the stresses in all the nodes of each of the six lumbar discs (~20,000 nodes per disc) as a function of mechanical traction level. It can be seen that the internal stresses developed in the lumbar discs exhibit a range of variability between 0.075 and 1.7 MPa, depending on the BMI and traction level, and the internal stresses in the disc are maximal in the normal BMI model and decrease as the BMI increases.

Since the ceramics 11 start to touch the lower back for TL4, the stress in the model remains close to the zero value below TL4. The internal stresses developed in the lumbar discs exhibit a range of variability between 0.075 and 1.7 MPa, depending on the BMI and traction level (TL5-TL9). The normal BMI model exhibits the lowest stress in the T12-L1 disc (~0.35 MPa), followed by the L5-S disc (~0.8 MPa). A similar level of maximal stresses was found in the L1-L2 and L4-L5 discs (~1.2 MPa), a little higher in the L3-L4 disc (~1.5 MPa) and the highest stresses were observed in the L2-L3 disc (~1.8 MPa). The apparent increase on stresses as a function of traction level at the different lumbar discs is nonlinear, possibly due to the complex/inhomogeneous deformation of the several tissues considered in the model and the morphology/curvature of the spine, even though the tissues mechanical properties were defined using linear elastic models. The presence of fat tissue in the posterior aspect of the lower back reduces the magnitude of the stresses seen in the intervertebral discs. The overweight BMI model exhibit similar trends in disc stresses when compared to the normal BMI model, but with stress magnitude reduced by 10-20% approximately. An equivalent behavior is recognized for the moderate and severe obese BMI models, but with a stress magnitude reduced by about 50 and 75%, respectively. This quantitative result represents a cause-effect relationship between the mechanical traction of the massage bed and the stress relief in each lumbar disc. In general, the L2-L3 disc was the one with the highest stresses, and the T12-L1 disc had the lowest stresses. These curves confirmed the qualitative observation in FIG. 8 indicating that the internal stresses in the disc are maximal in the normal BMI model and decrease as the BMI increases.

For example, assuming that the user may be injured when the stress applied to the discs is 0.1 MPa, depending on the user's body type, the traction level that can be used is determined, and if this level is exceeded, the user can be warned. In addition, since the levels to be used vary according to the position of the disk, it is possible to provide a suitable traction level to the user by reflecting this.

Figure 9:
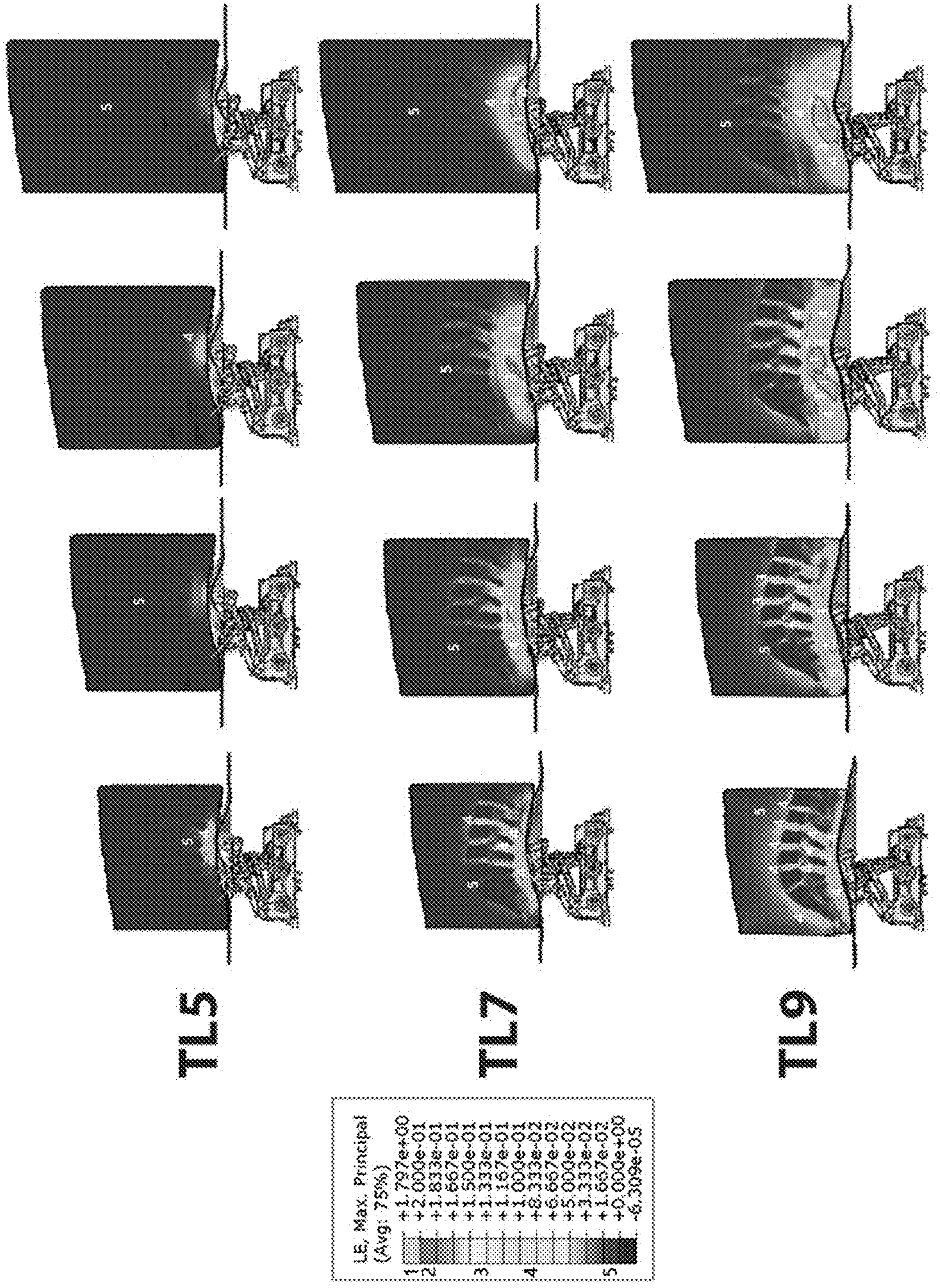
FIG. 9 is a view showing 3D stress for different BMI models, (a) shows the stress at traction levels 5, 7 and 9 for normal BMI user model, (b) shows the stress at traction levels 5, 7 and 9 for an overweight BMI user model, (c) shows the stress at traction levels 5, 7 and 9 for moderate obese BMI user model, and (d) shows the stress at traction levels 5, 7 and 9 for severe obese BMI user model.

FIG. 9 is a diagram showing 3D stress for different BMI models, (a) shows the stress at traction levels 5, 7 and 9 for normal BMI user model, (b) shows the stress at traction levels 5, 7 and 9 for an overweight BMI user model, (c) shows the stress at traction levels 5, 7 and 9 for moderate obese BMI user model, and (d) shows the stress at traction levels 5, 7 and 9 for severe obese BMI user model. Although the maximal strains in the intervertebral discs are presented in the normal BMI model at the highest traction level, it can be seen that the fat and soft tissues in the moderate and extreme obese models deform the most and shield the intervertebral discs from the strains.

The behavior of mechanical strains is equivalent to stresses in all tissues and models, as a function of traction level and BMI. FIG. 9 shows 3D strain on different BMI models: normal, overweight, moderate obese and extreme obese (column panels) at traction levels 5, 7 and 9 (row panels). Similar to the stresses result, the strains in all models for the TL4 or lower are practically zero, since the ceramics 11 touch the lower back tissues when the ceramics 11 move from TL4 to TL5. At TL5 we can readily observe deformation of the lower back. It can be seen that the maximal strains in tissues are presented in the normal BMI model at the highest traction level. However, it can be seen that the fat and soft tissues in the moderate and extreme obese models deform the most and the stress applied to the intervertebral discs is reduced from such deformation.

Figure 10:
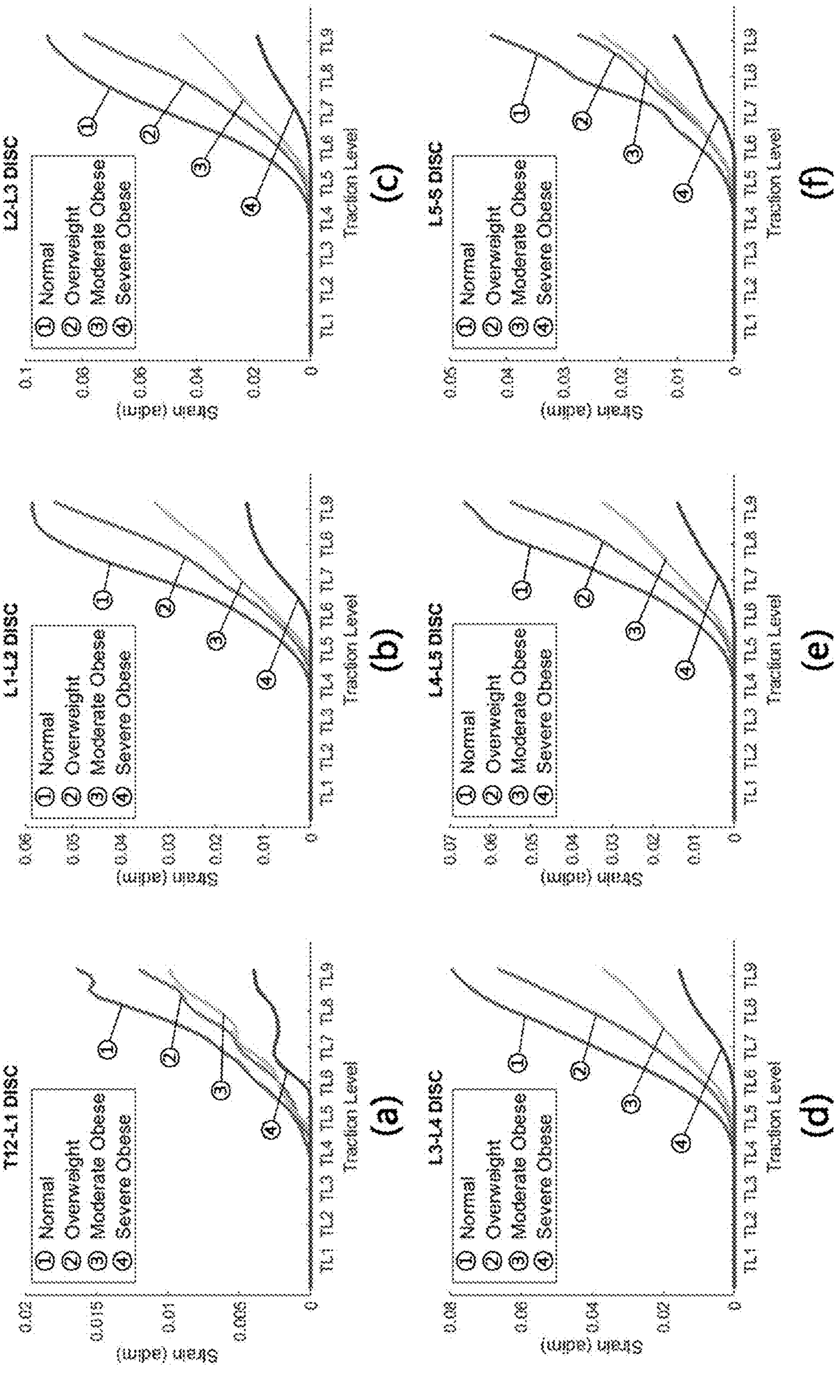
FIG. 10 is a view quantitatively comparing strains for different BMI models, (a) to (f) are views showing the deformation according to the traction level (TL1-9) for each position of each lumbar disc, classified according to BMI models (normal, overweight, moderate obese, and severe obese).

FIG. 10 is a diagram quantitatively comparing strains for different BMI models, (a) to (f) are views showing the deformation according to the traction level (TL1-9) for each position of each lumbar disc, classified according to BMI models (normal, overweight, moderate obese, and severe obese). The strains developed in the lumbar discs exhibit a range of variability between 0.005 and 0.1, depending on the BMI and traction level. The strains in the disc are maximal in the normal BMI model and decrease as the BMI increases.

As shown in FIG. 10, the approach to quantify the average strain level in the intervertebral discs is similar to the one described earlier for measurement of internal stresses. Overall, it can be seen that at TL9, the average strains range from 0.004 to 0.1, respectively, but vary depending across the different discs. In particular, these results indicate that the L2-L3 disc is the one with the highest deformation (up to 0.1% deformation), and the T12-L1 disc has the lowest strains. The curves for the different discs are indeed similar to those obtained for the stresses, and the trends are thus similar too. The maximal strains in the T12-L1 disc are the smallest among all the lumbar discs (~0.018), followed by the L5-S disc (~0.045). The maximal strains are larger in the L1-L2 disc (~0.06), the L4-L5 disc (~0.07) and the L3-L4 disc (~0.08), and are maximal in the L2-L3 disc, reaching a strain of about 0.1. Similar to the stresses, the strains in the overweight BMI model is 10-20% lower than in the normal BMI model. The moderate obese BMI model has about 50% lower strains when compared to the normal BMI model, and the severe obese BMI model shows ~75% lower strains than the normal model. Thus, these curves also confirm that the internal strains in the disc are the highest in the normal BMI model and decrease as the BMI increases.

For example, assuming that the user can be injured when the deformation of the disk is 0.05, the traction level that can be used is determined, and if this level is exceeded, the user can be warned. In addition, since the levels to be used vary according to the position of the disk, it is possible to provide a suitable traction level to the user by reflecting this.

In this case, calculating a stress applied to the user's body and a strain of the user's body in a process of pressurizing the user's body (Step 400) may comprise visualizing the stress and the strain of the user's body. The user's body may be any one or more parts of the user's body, such as the calculated skin, muscle, vertebrae, intervertebral disc.

In addition, the step of calculating a stress applied to the user's body and a strain of the user's body in a process of pressurizing the user's body (Step 400) may be a step of calculating the stress applied to the user's body and the strain of the user's body while the user's body is strained along a length direction X as the ceramic of the spinal thermal device 10 rises along the height direction Z. That is, the stress applied to the user's body and the strain of the user's body are calculated while the user's body is strained along a length direction X through the posteroanterior traction.

In this case, the step of calculating the stress applied to the user's body and the strain of the user's body in a process of pressurizing the user's body (Step 400) may be a step of calculating the stress and strain of a portion corresponding to the depth of the user's spine while the user's body is strained along a length direction X as the ceramic of the spinal thermal device rises along the height direction Z. For example, since the user's spine and the muscle surrounding the spine (e.g., erector spinae muscle) are located in a portion corresponding to the depth of 3 cm from the skin surface of the normal BMI user, the stress and the strain of the portion may be calculated to provide an optimal traction effect.

Meanwhile, the step of converting the strain value of the user's body to the degree of traction (Step 500) may further include a step of correcting the strain value of the user's body by reflecting the spine distance data for each body position of the user. For example, the spine distance data for each body position the user may be obtained through various techniques such as CT, MRI, and the degree of traction that is more accurate may be derived when the strain value of the body of the user is corrected in this manner, and the set value of the spinal thermal device 10 that is suitable for the user may be derived.

In addition, the step of calculating the stress and the strain of the user's body may be include a step of calculating the stress and the strain of the user's body through a dynamic explicit formulation.

In this case, the set of the setting the set value of the spinal thermal device may be a step of setting a ceramic 11 temperature, a ceramic 11 height, and a heating element temperature, and may be changed depending on a thermal massage mode selected by the user.

Meanwhile, after the step of visualizing the degree of traction of the user's body, the method may further include a step of deriving the set value for obtaining an optimal traction effect within a range of the set ceramic 11 temperature, ceramic 11 height, and heating element temperature. That is, by visualizing the degree of traction of the user's body, the set value is derived so as to obtain a degree of traction suitable for the user.

In this case, the step of deriving a set value for obtaining an optimal traction effect may be a step of deriving the set value for obtaining the optimal traction effect for each user's body type according to a change in structure according to the user's body type. That is, since the degree of traction varies according to a BMI value, and at the same time, whether there is a risk of injury may be varied, the optimal degree of traction needs to be derived depending on the BMI value, and when the degree of traction is reflected into the spinal thermal device 10, the optimal traction effect may be provided to various users and precautions can be transmitted so that the user may avoid injury during the thermal massage process.

As described above, in the method for predicting the safety and effectiveness of the spinal thermal device according to the embodiment of the present disclosure, the traction effect may be optimized according to the user's body shape by generating the 3D structure data of the user's body and the 3D structure data of the spinal thermal device 10, calculating a stress applied to the user's body and a strain rate of the user's body during the operation of the spinal thermal device 10 according to the set value, and then converting the calculated stress applied to the user's body and the strain of the user's body into the degree of traction, and thus the safety and effectiveness of the spinal thermal device 10 may be predicted.

Logical blocks, modules or units described in connection with embodiments disclosed herein can be implemented or performed by a computing device having at least one processor, at least one memory and at least one communication interface. The elements of a method, process, or algorithm described in connection with embodiments disclosed herein can be embodied directly in hardware, in a software module executed by at least one processor, or in a combination of the two. Computer-executable instructions for implementing a method, process, or algorithm described in connection with embodiments disclosed herein can be stored in a non-transitory computer readable storage medium.

Although the present disclosure has been described above, the spirit of the present disclosure is not limited by the embodiments presented in the specification, and those skilled in the art who understand the spirit of the present disclosure may easily propose other embodiments by adding, modifying, deleting, adding, etc., elements within the same spirit, but the spirit of the present disclosure is also given.

| | |
|---|---|
| 10 | spinal thermal device |
| 11 | ceramic |
| 12 | driving unit |
| 13 | support unit |
| 13a | first support member |
| 13b | second support member |
| X | length direction |
| Y | width direction |
| Z | height direction |

What is claimed is:

1. A method for predicting safety and effectiveness of a spinal thermal device using a computer, the method comprising:

generating three-dimensional structure data of a user's body;

generating three-dimensional structure data of the spinal thermal device;

setting an initial set value of the spinal thermal device comprising a ceramic temperature, a ceramic height, and a heating element temperature;

calculating, using a dynamic explicit formulation and based on the three-dimensional structure data of the user's body and the three-dimensional structure data of the spinal thermal device, a stress applied to the user's body and a strain of the user's body during a process of applying posteroanterior traction as a ceramic of the spinal thermal device rises along a height direction to pressurize the user's body according to the initial set value;

converting a strain value of the user's body to a degree of traction applied to an intervertebral disc of the user, wherein converting comprises correcting the strain value of the user's body by reflecting spine distance data for each body position of the user;

determining, based on the degree of traction, whether the initial set value exceeds a safety threshold associated with injury risk; and outputting control information, including warning information, that adjusts a set value for operation of the spinal thermal device to within a safe operating range based on the determination.

2. The method of claim 1, further comprising visualizing the stress and the strain of the user's body or the degree of traction of the user's body.

3. The method of claim 1, wherein calculating comprises calculating the stress applied to the user's body and the strain of the user's body while the user's body is strained along a length direction as the ceramic of the spinal thermal device rises along the height direction.

4. The method of claim 1, wherein calculating comprises calculating the stress and strain of a portion corresponding to a depth of the user's spine while the user's body is strained along a length direction as the ceramic of the spinal thermal device rises along the height direction.

5. The method of claim 1, wherein calculating comprises calculating the stress and the strain of the user's body through a dynamic explicit formulation.

6. The method of claim 1, further comprising deriving the set value for obtaining an optimal traction effect within a range of the set ceramic temperature, ceramic height, and heating element temperature.

7. The method of claim 6, wherein deriving comprises deriving the set value for obtaining an optimal traction effect for each user's body type according to a change in structure according to the user's body type.

8. The method of claim 1, wherein the three-dimensional structure data of the user's body is three-dimensional structure data classified into skin, subcutaneous fat, soft tissue, muscles, vertebrae, intervertebral disc, epidural fat, cerebrospinal fluid, and spinal cord.

* * * * *